United States Patent [19]
Carol

[11] Patent Number: 5,163,430
[45] Date of Patent: Nov. 17, 1992

[54] METHOD AND APPARATUS FOR PERFORMING STEREOTACTIC SURGERY

[75] Inventor: Mark P. Carol, Cooperstown, N.Y.
[73] Assignee: Medco, Inc., Cinnaminson, N.J.
[21] Appl. No.: 515,429
[22] Filed: Apr. 27, 1990
[51] Int. Cl.⁵ .............................................. A61B 19/00
[52] U.S. Cl. ................................ 128/653.1; 606/130; 378/20
[58] Field of Search ...................... 128/653.1; 606/130; 378/20, 208

[56] References Cited

U.S. PATENT DOCUMENTS

| | | |
|---|---|---|
| 2,697,433 | 12/1954 | Zehnder . |
| 3,457,922 | 7/1969 | Ray . |
| 4,228,799 | 10/1980 | Anichkov et al. ................ 606/130 |
| 4,583,538 | 4/1986 | Onik et al. ..................... 128/653 R |
| 4,592,352 | 6/1986 | Patil .............................. 606/130 |
| 4,608,977 | 9/1986 | Brown ............................ 606/130 |
| 4,638,798 | 1/1987 | Sheldon et al. ................. 606/130 |
| 4,723,544 | 2/1988 | Moore et al. .................... 606/130 |
| 4,805,615 | 2/1989 | Carol ............................. 606/130 |
| 4,955,891 | 9/1990 | Carol ............................. 606/130 |

FOREIGN PATENT DOCUMENTS

| | | | |
|---|---|---|---|
| 2094590 | 9/1982 | United Kingdom | ............... 606/130 |

OTHER PUBLICATIONS

"Instruction Manual for the BRW Brown-Roberts-Wells CT Stereotaxic System"; 1983; Radionics, Inc.
"Todd-Wells Manual of Stereotaxic Procedures", Edwin M. Todd, M.D., 1967.
"The PTM®Vaxiom™ Stereotactic System"; 1983; PMT Corporation.
"Technical Sheet #21"; 1983; DAP II Brain Biopsy Needle Guide; Ad-Tech Medical Instrument Corporation.
"Wells Stereotaxic Guides"; Rand-Wells Pallidothalamectomy Guide; 1 page; Undated.
"A Plastic Ball-and-Socket Type of Stereotactic Director"; 1958; George Austin, M.D. and Arnold Lee, A.B.
"Simple Plastic Stereotactic Unit for Use in the Computed Tomographic Scanner" 1983; Walter J. Levy, M.D., Neurosurgery vol. 13, No. 2.
"Trent Wells, Inc. Stereotaxic Instruments for Surgery and Research"; 1973.
"Riechert-Mundinger Stereotactic Apparatus"; Peter Dyek, undated.

*Primary Examiner*—Kyle L. Howell
*Assistant Examiner*—Krista M. Pfaffle
*Attorney, Agent, or Firm*—Ben D. Tobor

[57] ABSTRACT

A method and apparatus for performing stereotactic surgery upon a target within a skull establishes a first, predetermined geometric relationship between a skull mount fixture mounted on the skull and a scanning table surface upon which the skull is supported; and that geometric relationship is duplicated by a displacement bar mounted upon the skull mount fixture.

17 Claims, 5 Drawing Sheets

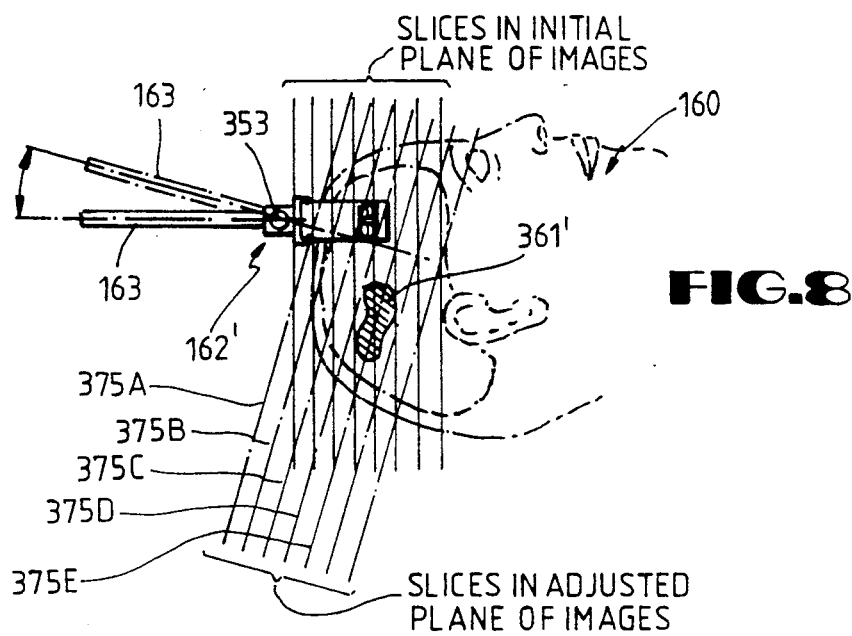
FIG. 8
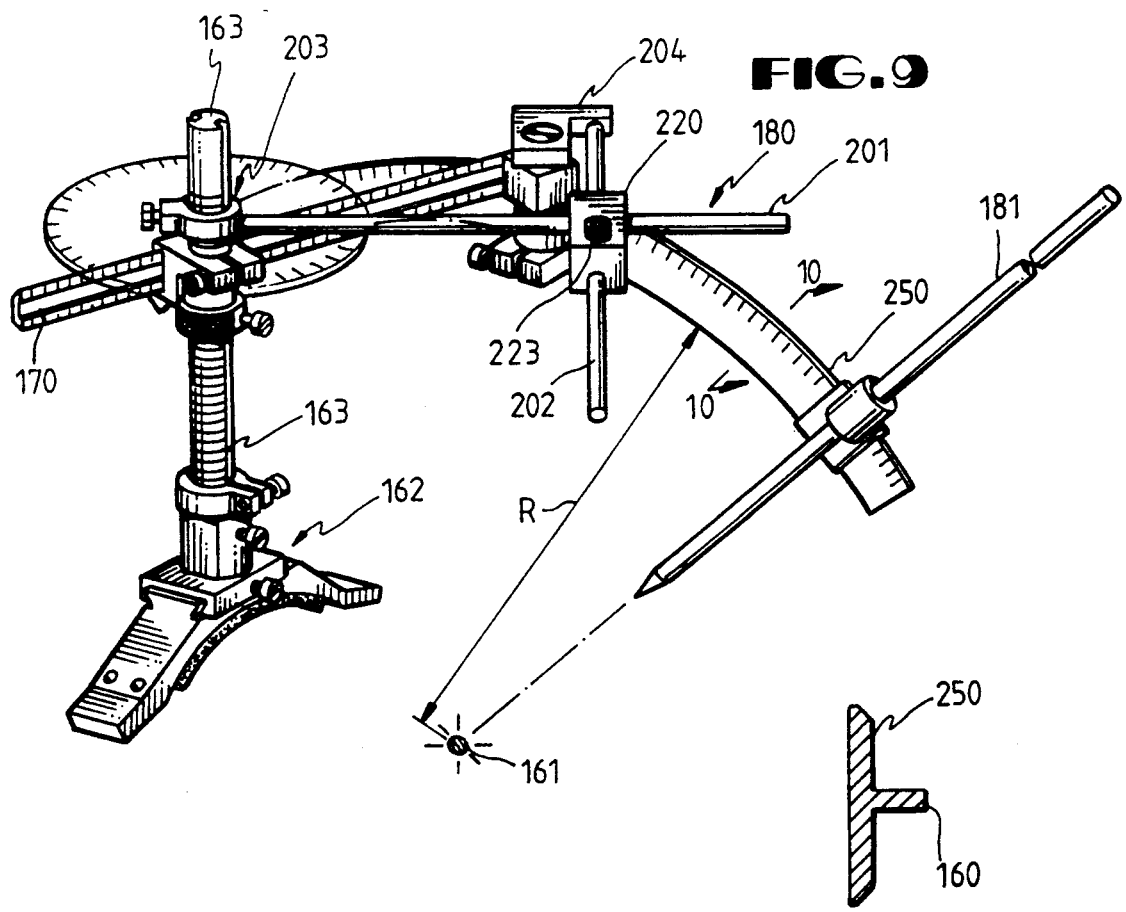
FIG. 9
FIG. 10

METHOD AND APPARATUS FOR PERFORMING STEREOTACTIC SURGERY

FIELD OF THE INVENTION

The invention relates to a method and apparatus for performing stereotactic surgery with a medical instrument upon a target within a skull.

DESCRIPTION OF THE PRIOR ART

One of the ongoing interests of neurosurgeons is the practice of stereotactic surgery; gaining precise access to a specific point in the cranium through the application of an external three-dimensional coordinate system. Much time and effort has gone into the development of instrumentation for implementing such an approach to the human brain. With the development of computerized tomographic ("CT") scanning, and its precise imaging, stereotactic surgery is becoming the diagnostic and therapeutic procedure of choice for many disorders involving the intracranial cavity.

CT scanning produces an image representing a "slice" of brain tissue displayed with anatomical accuracy. The series of "slices", which constitute the complete CT study, represent a three-dimensional picture of the brain, defining the relationship of neurological structures or accurately localizing lesions. CT scanning has allowed physicians to visualize the brain directly, thus making identification of anatomical and pathological areas of interest much more precise, and thus much more accessible to the precise mechanics of stereotactic surgery. Mating CT scanning and stereotactic surgery involves a coordinate transformation from the two-dimensional space of CT scanning to the three-dimensional space of stereotactic surgery.

Although there has been a wide range of methods and devices designed to implement such a coordinate conversion, most of the devices have had a similar conceptual approach, wherein the resulting devices have left stereotactic surgery as being perceived as an esoteric, cumbersome, expensive, and time consuming procedure.

These prior art devices and methods typically utilize a bulky frame mounted to the patient's skull by four pins or screws. Such devices have been found to be quite accurate and reliable and have allowed targets within a skull to be accessed with an accuracy of 1 mm. or less. They have allowed small, relative inaccessible tumors to be biopsied with minor morbidity and practically absent mortality. These devices have also given surgeons a means of biopsying accessible tumors that are radiosensitive without the need for a formal craniotomy, a procedure that carries a much higher mortality and morbidity than stereotactic surgical procedures. In addition, such devices have provided a means for implementing new modalities for treating hematomas and abscesses, as well as the placement of radioisotopes and chemotherapeutic agents in the treatment of malignant brain tumors.

Despite these advances, there are characteristics of current stereotactic instruments which have severely limited their potential widespread application. The performance of careful stereotactic procedures on a regular basis with the prior art systems available requires much operating room time to be wasted during the procedure. Processing of X-ray pictures, target point calculations, and cumbersome mechanical adjustments on stereotactic frames add time to the operation. The inability of these systems to be reused on the same patient without recalculating target points also adds to their inefficiency. Although the prior art stereotactic instruments are adequate for reaching a single intracranial target point, rapid access to multiple targets during a procedure is inconvenient. Furthermore, the prior art devices are extremely expensive and are quite complicated to employ, thereby making their appeal to the surgeon in private practice quite limited. Some of the prior art systems require modifications of existing CT scanning software, or alternatively, require software generated coordinates determined from a hand-held calculator as part of the system. The frame required by these prior art devices require fixation to the skull of the patient, typically via four screws, whereby the frame is quite cumbersome and uncomfortable. Additionally, the frame cannot be left on the patient's head if the same procedure is to be repeated at a later date. If subsequent stereotactic procedures are to be performed, the frame must be reapplied at the time of the second procedure, including the step of again using a CT scanner to calculate the coordinates of the target point within the skull.

Many, if not all, of the foregoing disadvantages and problems associated with prior art devices and methods were solved by the method and apparatus for performing stereotactic surgery taught in U.S. Pat. No. 4,805,615, wherein a compact, easy to use positioning fixture is used in conjunction with a phantom fixture. The positioning fixture of that patent utilized a ball and socket approach. Although the method and apparatus taught in that patent constituted a significant advance in the art, there are still certain disadvantages associated with the use of the method and apparatus taught in that patent.

Because of the use of the ball and socket approach in the method and apparatus of that patent, it is an angular system, whereby the target within the skull is reached by passing a probe through the ball along a path which represents a compound angle with respect to the frame of reference of the system, which is the plane of the imaging process. In order to move the probe, or medical instrument, in any given direction a prescribed amount, a new compound angular trajectory must be calculated. Linear offset applications are presently a part of many stereotactic procedures, and they require the ability to move the target point around inside the skull in a linear fashion in any plane. One of these linear offset applications is in the field of functional procedures. The targets for many of these procedures are referenced on the AC PC line, as are standard physiologic and anatomic atlases. Although with current stereotactic systems, the approximate location of the target within the skull can be generated from CT scanning or magnetic resonance ("MR") imaging, physiologic verification based upon anatomic parameters are needed prior to lesioning the target. This requires offsetting the target in a linear fashion, in any plane, such as the linear coordinates of the target along the X, Y, and Z axes, until the precise lesion location is identified.

Another example of linear offset applications is if the surgeon is performing a thalamotomy, wherein a lesion is made in the thalamus for functional or motor disorders, and the surgeon may find through electrical stimulation that the initial target point within the skull was off by 2 mm AP direction. It is desirable to have a system which, without the need for recalculating the location of the target within the skull, could be adjusted so that the new target point would vary by 2 mm in only the AP direction.

Another disadvantage associated with the method and apparatus of U.S. Pat. No. 4,805,615, as well as many, if not all, of the other prior art methods and apparatus, is that it is necessary to use a phantom fixture in order to determine the trajectory of a medical instrument to the desired target within the patient's skull. It is typically necessary to perform several, rapid, but somewhat cumbersome manipulations and transfers of the component pieces of the equipment between the patient and the phantom fixture in order to generate the trajectory to the desired target. Each of these transfers of equipment represents a potential source of error in usage of the system. Additionally, the required use of a phantom fixture increases the cost, size, and weight of the stereotactic system.

Accordingly, prior to the development of the present method and apparatus for performance stereotactic surgery, there has been no method and apparatus for performing stereotactic surgery which: is compact, inexpensive, easy to use, precise, and comfortable; does not require a bulky skull mounted frame; does not require the use of a phantom fixture or a ball and socket positioning fixture; and permits linear offset applications to be conducted. Therefore, the art has sought a method and apparatus for performing stereotactic surgery which: does not require a skull mounted frame; is compact, inexpensive, easy to use, precise and comfortable; does not require the use of a phantom fixture or a ball and socket positioning fixture; and permits linear offset applications to be performed.

SUMMARY OF THE INVENTION

In accordance with the invention, the foregoing advantages have been achieved through the present method and apparatus for performing stereotactic surgery. The method for performing stereotactic surgery, in accordance with the present invention, includes the steps of: establishing a first, predetermined geometric relationship between a skull mount fixture, attached to both the skull and to a support surface upon which the skull is dispersed, and the support surface; scanning the skull to produce images of the skull mount fixture and the target within the skull; determining the linear coordinates of the target along X, Y, and Z axes with respect to the skull mount fixture; disposing a displacement bar, having first and second ends, upon the skull mount fixture to establish a second, predetermined geometric relationship therebetween, which is identical to the first, predetermined geometric relationship; disposing the first end of the displacement bar directly over the target in the skull; associating a means for guiding a medical instrument with the first end of the displacement bar; and inserting the medical instrument through the medical instrument guide means, whereby the medical instrument will intersect the target in the skull.

A feature of the present invention is that the first, predetermined geometric relationship is the skull mount fixture disposed in a plane which lies perpendicular with respect to the longitudinal axis of the support surface; and the second, predetermined geometric relationship is the displacement bar disposed in a plane parallel with the plane in which lies the skull mount fixture, whereby the scanned images all lie in planes parallel with the planes in which lie the skull mount fixture and displacement bar.

Another feature of the present invention is the step of securing in a first position the first end of an elongate post, having first and second ends, to the skull mount fixture and releasably securing the displacement bar with respect to the second end of the post along the post; the post, in the first position, being disposed in a plane which is perpendicular to the planes in which lie the skull mount fixture and the displacement bar.

Another feature of the present invention is the step of utilizing two cooperating guide bars to dispose the first end of the displacement bar directly over the target in the skull, one of the guide bars being associated with the linear coordinate of the target along the X axis, and the other guide bar being associated with the linear coordinate along the Y-axis. A further feature of the present invention is the step of movably mounting an arc bar, having a fixed radius of curvature, to the first end of the displacement rod; and movably mounting the medical instrument guide means upon the arc bar, whereby the target in the skull may be intersected by a medical instrument that has the capability to pass through the skull from a variety of different locations on the surface of the skull, depending upon the locations of the arc bar with respect to the displacement bar and the medical instrument guide means with respect to the arc bar. Another feature of the present invention includes the step of angularly offsetting the post from its first position to a second position, the displacement bar lying in a plane which is perpendicular to the angularly offset post, whereby the location of a target may be determined, which target lies in a plane which is not parallel to the planes in which lie the scanned images.

In accordance with the invention, the foregoing advantages have also been achieved through the present system for performing stereotactic surgery. The system for performing stereotactic surgery, in accordance with the present invention, may include: a skull mount fixture, having associated therewith a means for attaching the skull mount fixture to both the skull and to a support surface upon which the skull is disposed; a straight, elongate displacement bar, having first and second ends, movably mounted upon the skull mount fixture for both longitudinal and rotational movement with respect to the skull mount fixture, the longitudinal axis of the displacement bar being disposed in a plane which lies parallel to the plane in which lies the longitudinal axis of the skull mount fixture: and a means for guiding a medical instrument associated with the first end of the displacement bar.

Another feature of the system in accordance with the present invention is that the skull mount fixture may further include an elongate post having first and second ends, the first end being secured to the skull mount fixture, the post lying in a plane which is perpendicular to the planes in which lie the longitudinal axis of the skull mount fixture and the displacement bar, the displacement bar being releasably secured with respect to the second end of the post. An additional feature of the present invention is that the system may include two cooperating guide bars, each guide bar having first and second ends, the first end of one guide bar being fixedly secured to the post and the first end of the other guide bar being movably mounted to the first end of the displacement bar; the guide bars being interconnected to one another intermediate the first and second ends of each guide bar; the guide bars being movable with respect to each other, whereby movement of the guide bar mounted to the first end of the displacement bar causes the displacement bar to move longitudinally and rotationally with respect to the post.

An additional feature of the system of the present invention is that an arc bar, having a fixed radius of curvature may be movably mounted to the first end of the displacement bar; and the medical instrument guide means may be movably mounted upon the arc bar. A further feature of the present invention is that a protractor plate may be secured to the post to determine the angular orientation of the longitudinal axis of the displacement bar with respect to the longitudinal axis of the post.

In accordance with the invention, the foregoing advantages have also been achieved through another method for performing stereotactic surgery. This other method for performing stereotactic surgery, in accordance with the present invention, includes the steps of: establishing a first, predetermined geometric relationship between a skull mount fixture, attached to both the skull and to a support surface upon which the skull is disposed, and the support surface; scanning the skull to produce images of the skull mount fixture and the target within the skull; determining the linear coordinates of the target along X, Y, and Z axes with respect to the skull mount fixture; disposing a rectangular shaped frame structure upon the skull mount fixture to establish a second predetermined geometric relationship therebetween, which is identical to the first-predetermined geometric relationship; movably mounting two straight, elongate first and second coordinate bars to the frame structure, the coordinate bars being disposed perpendicular to each other and the first coordinate bar being disposed in the plane parallel with the plane in which lies the skull mount fixture; movably mounting a means for guiding a medical instrument on an arc bar having a fixed radius of curvature, the arc bar being movably mounted on the first coordinate bar and inserting the medical instrument through the medical instrument guide means where, whereby the medical instrument will intersect the target in the skull.

A further feature of the present method, in accordance with the present invention, includes the step of rotating the frame structure with respect to the skull mount fixture, whereby the location of a target may be determined, which target lies in the plane which is not parallel to the plane which lie the scanned images.

In accordance with the invention, the foregoing advantages have also been achieved through another system for performing stereotactic surgery. The system for performing stereotactic surgery, in accordance with the present invention, may include: a skull mount fixture having associated therewith a means for attaching the skull mount fixture to both the skull and to a support structure upon which a skull is disposed: a rectangular shaped frame structure including means for attaching the frame structure to the skull mount fixture, the frame structure lying in a plane which is parallel with the plane in which lies the skull mount fixture; two straight, elongate, first and second, coordinate bars movably mounted to the frame structure, the coordinate bars being disposed perpendicular to each other, and the first coordinate bar is disposed in a plane which is parallel with the plane in which lies the skull mount fixture: and means for guiding a medical instrument movably mounted on an arc bar, having a fixed radius of curvature, the arc bar being movably mounted on the first coordinate bar. An additional feature of the system present invention is that the skull mount fixture may include means for rotably mounting the frame structure with respect to the skull mount fixture.

The method and apparatus for performing stereotactic surgery of the present invention, when compared with previously proposed prior art methods and apparatus, have the advantages of being: compact, inexpensive, easy to use, precise, and comfortable for the patient; does not require a skull mounted frame, a ball and socket positioning fixture, or a phantom fixture; and permits linear offset applications to be conducted.

BRIEF DESCRIPTION OF THE DRAWINGS

In the drawings:

FIG. 8 is a side view of a patient having the modified skull mount fixture of FIG. 5 disposed on the patient's skull, and illustrating the planes in which lie the scanned images, or "slices";

FIG. 9 is a perspective view of the system for performing stereotactic surgery in accordance with the present invention;

FIG. 10 is a cross-sectional view taken along line 10—10 of FIG. 9;

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

With reference to FIGS. 1, 6, 7, and 11, the method for performing stereotactic surgery with a medical instrument upon a target within a skull will be generally described. A patient's skull 160 is shown to have a target 161 therein which is desired to be treated. For example, target 161 could be a hematoma, abscess, or tumor.

Figure 1:
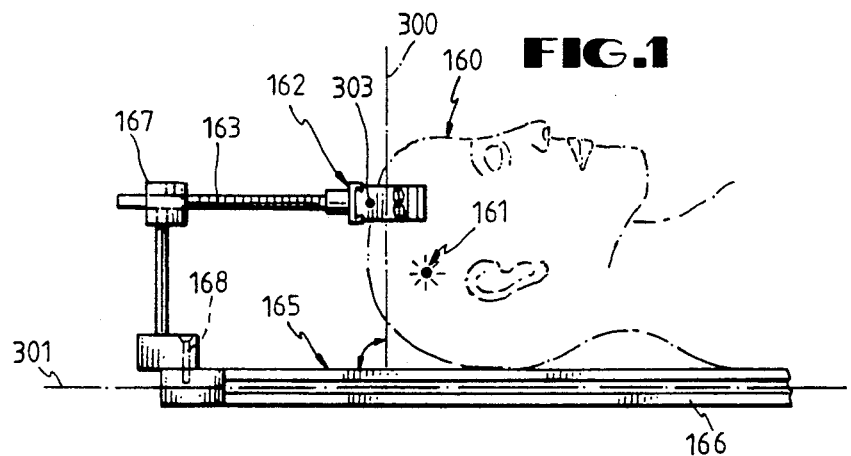
FIG. 1 is a side view of a patient disposed upon a support surface with a skull mount fixture of the present invention disposed on the patient's skull.
Figure 6:
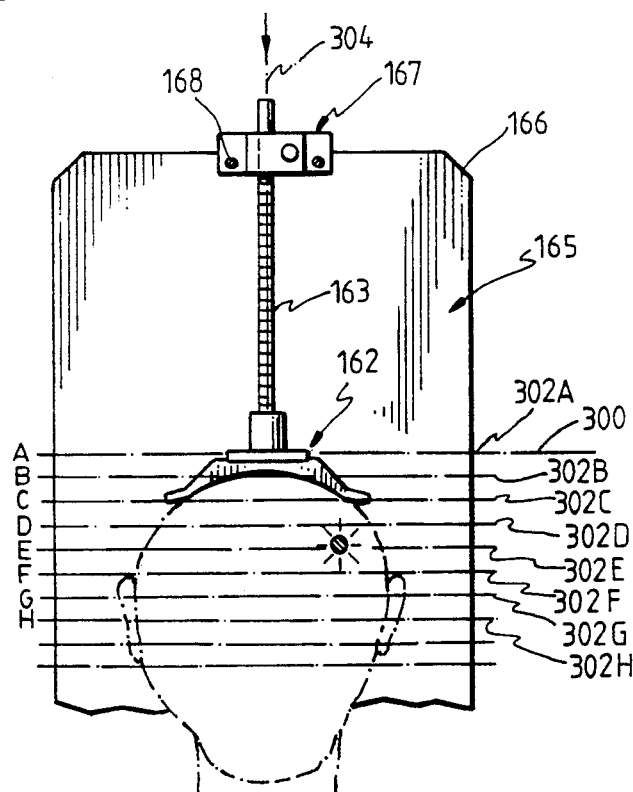
FIG. 6 is a top view of a skull mount fixture disposed upon a support surface, with the skull mount fixture being disposed on the patient's skull (shown in dotted lines), with the scanned images, or "slices", being illustrated.

With reference to FIGS. 1 and 6, a skull mount fixture 162 is attached to skull 160 in a manner to be hereinafter described in greater detail. Preferably, skull mount 162 is constructed in accordance with the present invention, as will be hereinafter described in greater detail. Preferably, the location upon skull 160 at which skull mount fixture 162 is attached to skull 160 is determined by the location of target 161 within skull 160 and skull mount fixture preferably straddles the centerline of the patient's skull, as seen in FIG. 6, and is disposed upon the top of patient's skull 160 as seen in FIG. 1. Preferably, skull mount fixture 162 is disposed on the parietal boss portion of the patient's skull 160. Thus, skull mount 162 may be disposed in the approximate position shown in FIG. 1, or alternatively, disposed in a lower position from that shown in FIG. 1. Skull mount fixture 162 may have a post or alignment rod, 163, associated therewith, which is disposed parallel with the centerline, longitudinal axis of a support surface 165, as will be hereinafter described in greater detail.

Figure 2:
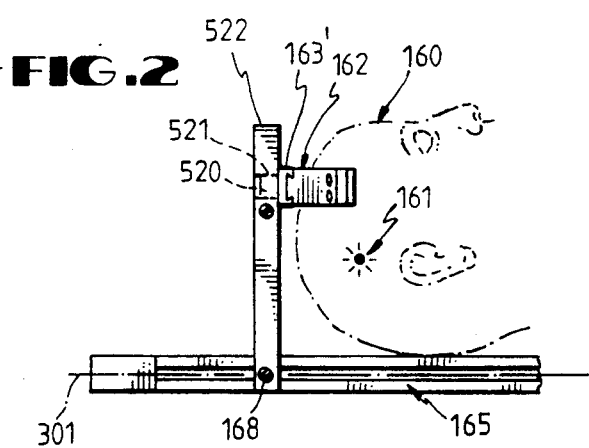
FIG. 2 is a side view of a patient disposed upon a support surface with another embodiment of a skull mount fixture of the present invention disposed upon this patient's skull.

With reference to FIGS. 1 and 2, the patient is laid upon a support surface 165, and skull 160 is thus disposed upon support surface 165. Typically, support surface 165 is a conventional, planar imaging table 166 which is used in connection with a conventional scanning device, such as a CT scanner. Alignment rod, or post, 163 is moved with respect to skull mount fixture 162, so that alignment rod, or post, 163 may mate with an upright bracket 167 which is secured to imaging table 166 in any suitable fashion, such as by a clamp or screws 168. With the skull mount fixture 162 and alignment rod 163 in the positions illustrated in FIGS. 1 and 6, a first, predetermined geometric relationship has been established between the skull mount fixture 162 and the support surface 165 upon which skull 160 is disposed. Preferably, this first, predetermined geometric relationship is with the skull mount 162 being disposed in a plane 300 which lies perpendicular with respect to the longitudinal axis 301 of the support surface 165.

With patient's skull 160 disposed upon support surface 165, as shown in FIGS. 1 and 6 and the skull mount fixture 162 being disposed in the first, predetermined geometric relationship with respect to support surface 165 and attached therebetween as by alignment rod 163 and bracket 167, the skull is then scanned by any suitable scanning device, such as a CT scanner, in a conventional manner. A radiopaque marker, or reference point, 303 (FIG. 7) is disposed in the center of the skull mount fixture 162, whereby the scanning procedure produces a series of images, or slices, of the skull 160, including the target 161 with respect to the skull mount fixture 162. As seen with reference to FIGS. 6 and 7, a plurality of scanned images, or slices, 302A-302H. . . are obtained because of the first, predetermined geometric relationship previously described. Skull mount fixture 162, including the marker, or reference point, 303 lies in plane 300 which plane also coincides with slice 302A. The target 161 lies in the plane of slice, or scanned image, 302E which plane, or slice 302E, is parallel to slice 302A, as is well known in the art. The distance between the different slices, or images, 302 is a predetermined distance depending upon the amount of movement of the imaging table 166 of the CT scanner.

Figure 7:
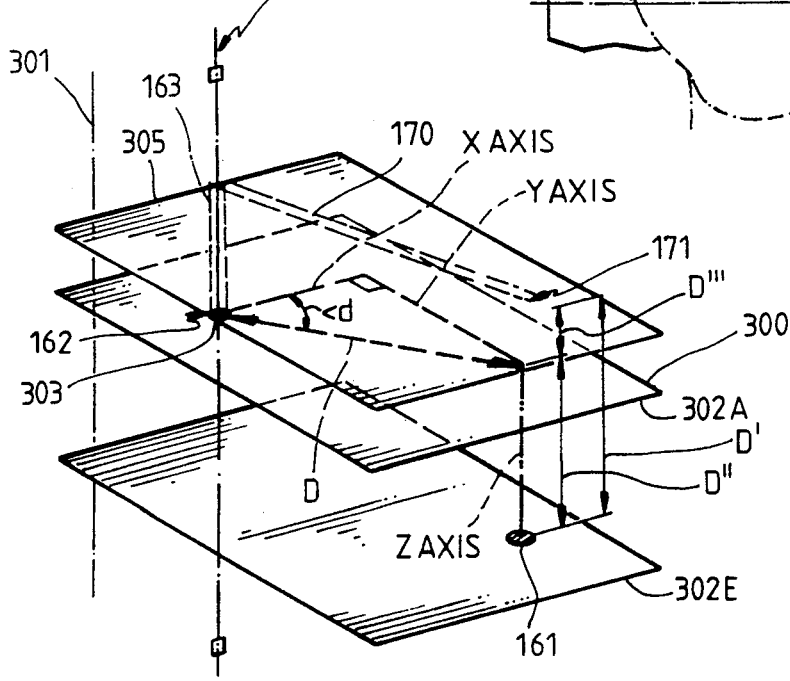
FIG. 7 is a perspective view illustrating the geometric relationships involved in the present invention.

Because the axis of imaging 304 of the CT scanner coincides with the longitudinal axis of the alignment rod, or post, 163 (FIGS. 6 and 7). the linear coordinates of the target 161 with respect to the skull mount fixture 162 along the X, Y, and Z axes, as illustrated in FIG. 7, can be readily determined by direct measurements from the various slices 302, and in particular slices 302A and 302E. The measurements along the X and Y axes can be directly measured from the various slices, or images, 302, and the linear coordinate along the Z axis is readily determined by the predetermined distance between the slices 302, as previously discussed.

After the linear coordinates of the target 161 with respect to the skull mount fixture 162 have been determined, a displacement bar 170, having first and second ends 171, 172 (FIG. 11) is disposed upon skull mount fixture 162 to establish a second, predetermined geometric relationship therebetween, which geometric relationship is identical to the first, predetermined geometric relationship. Preferably, the second, predetermined geometric relationship is with the displacement bar 170 disposed in a plane which is parallel with the plane 300 in which lies the skull mount fixture 162. As will be hereinafter described in greater detail, displacement bar 170 is preferably disposed upon skull mount fixture 162 as by movably mounting it to alignment rod, or post 163; the displacement bar 170 being mounted to post 163 perpendicular thereto, whereby since post 163 is disposed perpendicular to skull mount fixture 162, displacement bar 170 and skull mount fixture 162 are disposed to lie in parallel planes. Thus, both displacement bar 170 and skull mount fixture 162 each lie in planes which are perpendicular to longitudinal axis 301 of support surface 165 as seen in FIG. 7. Displacement bar 170 lies in plane 305, plane 305 being also parallel with the parallel planes in which lie the images, or slices 302A and 302E. The distance between plane 305 of displacement bar 170 and the plane, or slice. 302A in which lies skull mount fixture 162 would be dependent upon where along post 163 displacement bar 170 is disposed, as will be hereinafter described in greater detail. Accordingly, as seen in FIGS. 6 and 7, the scanned images, or slices 302A-H . . . will all lie in planes parallel with the planes in which lie the skull mount fixture 162 (plane 300, or slice, 302A) and the displacement bar 170 (plane 305).

The first end 171 of the displacement bar 170 is then disposed directly over the target 161 in the skull 160 as shown in dotted lines in FIG. 7. The displacement bar 170 can be disposed in the position shown in FIG. 7 in two different manners as will be hereinafter described in greater detail. After the first end 171 of displacement bar 170 has been disposed directly over the target 161 in the skull 160, a means for guiding 180 a medical instrument 181 (FIG. 9) is associated with the first end 171 of displacement bar 170. As will be hereinafter described in greater detail, two types of medical instrument guide means 180 may be utilized for guiding medical instrument 181. In both types, however, the medical instrument 181 will be inserted through the medical instrument guide means 180, until the medical instrument 181 intersects the target 161 in skull 160. With reference to FIG. 7, it is seen that the vertical distance from the first end 171 of displacement bar 170 to the target 161 is readily determined from knowing the spacing, or distance between, image, or slice, 302A and image, or slice, 302E, added to the distance between the reference point 303 on the skull mount fixture 162 and the vertical location of the displacement bar 170, along post 163. Knowing the distance D' between the first end 171 of displacement bar 170 and target 161, medical instrument 181 can be readily caused, in a conventional manner, to only travel that distance D' so that it will intersect target 161 in the desired manner.

Although it may be possible for the treatment of some targets 161, to directly mount displacement bar 170 upon skull mount fixture 162, it is preferred to utilize post 163, having first and second ends 175, 176, to support displacement bar 170 in its desired relationship with respect to skull mount fixture 162, so that the vertical spacing between skull mount fixture 162 and displacement bar 170 may be varied, as will be hereinafter described in greater detail. Preferably, first end 175 of post 163 is secured to skull mount fixture 162, and displacement bar 170 is releasably secured with respect to the second end 176 of the post 163, along the length of post 163. In this position, or first position, illustrated in FIGS. 9 and 10, as previously described, the post 163 is disposed in a plane which is perpendicular to the planes in which lie the skull mount fixture 162 and the displacement bar 170, as seen in FIG. 7, wherein post 163 is shown in phantom lines.

As previously discussed, the first end 171 of displacement bar 170 can be caused to be disposed directly above target 161 in two different manners. As seen in FIG. 7, the angular disposition or angle d, of target 161 with respect to reference point 303, along the X and Y axes can be directly determined from measuring linear X and Y coordinates and computing the angle d in accordance with the standard geometric formula angle d = arc tan X/Y. Alternatively, angle d can be directly measured using a protractor and measuring the angle from the scanned images 302A-E. Likewise, the distance D from the reference point 303 on skull mount fixture 162 to the target 161 can be directly measured from the scanned images, or alternatively, it is seen that the distance D is the hypotenuse of a right triangle as seen in FIG. 7. Thus, knowing the X coordinate and the Y coordinate of target 161, distance D can be determined from the geometric formula $X^2 + Y^2 = D^2$. Once the angle d and distance D have been determined, the first end 171 of displacement bar 170 is disposed over the target 161 in the following manner.

Figure 11:
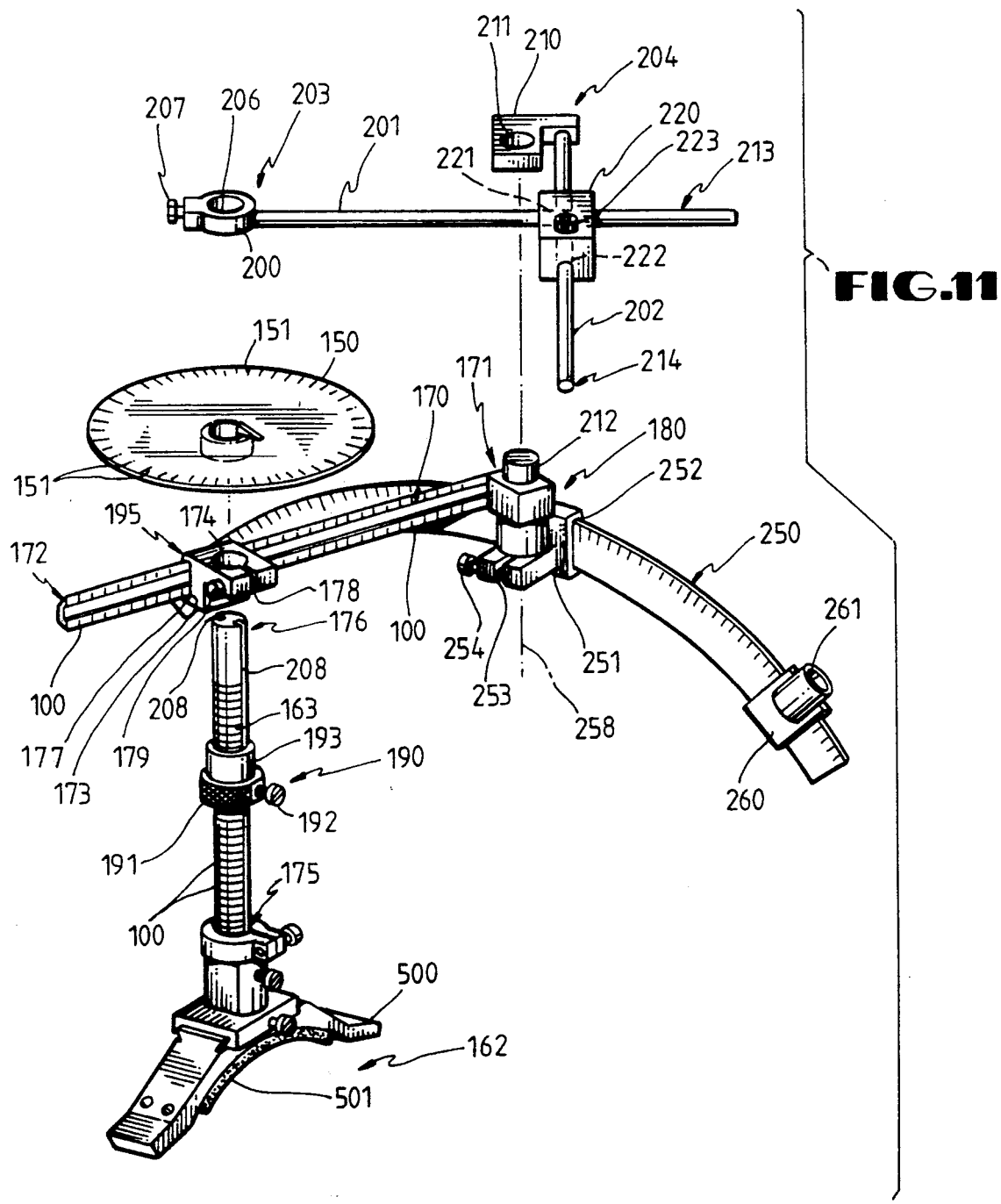
FIG. 11 is an exploded, perspective view of a system for performing stereotactic surgery in accordance with the present invention.

With reference to FIGS. 9 and 11, displacement bar 170 is disposed over the second end 176 of post 163. Over displacement bar is disposed a protractor 150 which may be fixedly secured to post 163. Protractor plate 150 has a plurality of angular markings 151. Preferably, displacement bar 170 is mounted to post 163 via a carrier block 173 which has a circular opening 174 formed therein to permit carrier block 173 to be slidably and rotatably received over the second end 176 of post 163. Carrier block 173 also preferably includes a groove 177 which cooperates with the cross-sectional configuration of displacement bar 170, whereby displacement bar 170 can slide with respect to carrier block 173. Any suitable means can be used to insure that displacement bar 170 is movable with respect to carrier block 173, and can be movably secured to post 163 via carrier block 173. A suitable, conventional, lockscrew (not shown) may be provided to releasably fix the disposition of displacement bar 170 with respect to carrier block 173.

Carrier block 173 is rotatable about post 163, in that the diameter of opening 174 is slightly larger than the diameter of post 163. Carrier block 173 is preferably provided with a slot 178 and a lockscrew 179 which spans slot 178, whereby tightening of lockscrew 179 causes slot 178 to close, which in turn causes the size of opening 174 to decrease. Accordingly, tightening of lockscrew 179 can cause carrier block 173 to not rotate about post 163.

Post 163 may also be provided with a first means for adjustably securing 190 the displacement bar 170 along the length of post 163 in order to vary the distance of the displacement bar 170 from the skull mount fixture 162. Preferably, the first adjustable securing means 190 is a lockable, depth stop 191 which is disposed about post 163 and includes a locking screw 192 to fixedly secure depth stop 191 at the desired location along the length of post 163. Depth stop 191 may include a cylindrical, upstanding bushing 193 which fits within opening 174 of carrier block 173. Carrier block 173, as previously described, provides a second means for securing 195 the displacement bar 170 to the post 163, whereby the distance from the first end 171 of the displacement bar 170 to the post 163 may be varied, as by sliding displacement bar 170 within carrier block 173, such sliding movement causing relative movement of the first end 171 of displacement bar with respect to post 163. Both displacement bar 170 and post 163 may have visual markings, or graduation lines, 100 formed or marked thereon to indicate lengths and distances.

With reference to FIGS. 9 and 10, it is seen that the first end 171 of displacement bar 170 can be caused to be disposed directly over target 161, as by causing displacement bar 171 to have the angular disposition, or angle d, relationship with respect to post 163, as by rotating displacement bar 170 with respect to post 163, and when the desired angle, angle d, has been measured from protractor plate 150, the angular, rotational movement of displacement bar 170 is prohibited by the tightening of lockscrew 179 of carrier block 173. The first end 171 of displacement bar 170 is then moved longitudinally with respect to carrier block 173, as by sliding displacement bar 170 with respect to carrier block 173, until the first end 171 of displacement bar 170 is disposed the previously measured, or computed, distance D from the post 163, at which time a conventional locking screw (not shown) is tightened to secure displacement bar 170 within carrier block 173.

The second method for disposing the first end 171 of displacement bar 170 directly over target 161 may also be accomplished by utilizing two cooperating guide bars 201, 202, as seen in FIGS. 9 and 11. One of the guide bars is associated with the linear coordinate of the target along the X axis, and the other guide bar is associated with the linear coordinate of the target along the Y axis. Guide bar 201 has a first end 203 which is fixedly secured to the post 163 and the first end 204 of guide rod 202 is movably mounted on the first end 171 of displacement bar 170. Preferably, the first end 203 of guide bar 201 has an end member 205 which has a circular opening 206 therein which slides over the second end 176 of post 163. End member 205 also preferably includes a lockscrew 207 which engages with a vertical keyway 208 which runs the length of post 163. Preferably, two vertical keyways 208 are provided in post 163, keyways 208 being disposed 180 degrees apart from one another. Thus, locking screw 207 engages in keyway 208, whereby guide bar 201 is fixedly secured to post 163, and guide bar 201 is disposed perpendicular to a plane in which lie both the skull mount fixture 162 and post 163.

The first end 204 of guide bar 202 is provided with a connector member 210 having a circular opening 211 which rests upon a cooperating, mating circular, raised boss 212 which may be provided at the first end 171 of displacement bar 170. The guide bars 201, 202 are preferably interconnected to one another intermediate the first ends 203, 204, and second ends 213, 214, of guide bars 201, 202. Preferably, guide bars 201, 202 are interconnected by a connector block 220 which has passageways 221, 222, disposed therein for sliding engagement with guide bars 201, 202, passageways 221, and 222 being staggered from one another in the vertical direction, so as to permit the passage of guide bars 201, 202 therethrough at a 90 degree angle with respect to one another.

With: the first end 203 of guide bar 201 fixedly secured to post 163; the first end 204 of guide bar 202 movably mounted on the first end 171 of displacement bar 170; and the guide bars being interconnected by connector block 220, it should be seen that movement of one guide bar 202 with respect to guide bar 201 will cause the first end 171 of displacement bar 170 to move, provided connector block 173 is not fixedly secured as by tightening lockscrew 179, to post 163, and displacement bar 170 is free to move within groove 177 of carrier block 173. It should also be seen from FIG. 9 that displacement bar 170 forms a variable length hypotenuse of a right triangle which has its variable sized legs formed by the portions of the guide bars 201, 202, disposed between the first ends 203, 204, of each guide bar 201, 202, and connector block 220. It should be noted that movement of one of the guide bars, 202, causes displacement bar 170 to move longitudinally with respect to post 163, as well as rotationally about post 163.

With reference to FIGS. 9 and 11, it should be noted that if no post 163 is utilized, and displacement bar 170, including carrier block 173, is disposed directly upon skull mount fixture 162, medical instrument guide means 180 could be provided by providing an opening (not shown) at the first end 171 of displacement bar 170, through which opening a medical instrument 181 could pass the desired distance D" (FIG. 7), whereby the medical instrument 181 would intersect target 161. Displacement bar 170 could be caused to be disposed directly over target 161 as by use of protractor plate 150, or by use of the guide bars 201, 202, as previously described.

Preferably, however, post 163 is disposed between skull mount fixture 162 and displacement bar 170. When post 163 is utilized, it is also preferable to movably mount an arc bar 250 which has a fixed radius of curvature R (FIG. 9) to the first end 171 of the displacement rod 170. The medical instrument guide means 180 may then preferably be movably mounted upon the arc bar 250, whereby the target 161 in the skull 160 may be intersected by a medical instrument 181. As seen in FIGS. 9 and 10, arc bar 250 is movably mounted to the first end 171 of displacement bar, as by a mounting block 251 which is rotably received within the first end 171 of displacement bar 170. Mounting block 251 also has a passageway 252 through which arc bar 250 may slide therethrough. Mounting block 251 has a construction similar to that of carrier block 173, whereby a slot 253 is provided with a locking screw 254 to permit the desired angular orientation of arc bar 250, with respect to displacement bar 170, to be locked into position. Likewise, a conventional locking screw (not shown) may be provided adjacent passageway 252 to engage arc bar 250 to restrain its movement through passageway 252. Instrument guide means 180 may preferably be provided by a guide mounting bracket 260 which includes a cylindrical medical instrument guide passageway 261, guide mounting bracket being slidable and movable along arc bar 250. Guide mounting bracket 260 may also be provided with a conventional locking screw to fix the position of guide mounting bracket 260 at a desired location along arc bar 250. As seen in FIG. 10, arc bar 250 has a generally rectangular cross-sectional configuration, provided with a stiffening rib member 160, although it could have any other suitable cross sectional configurations.

With reference to FIGS. 9 and 11, by disposing the first end 171 of displacement bar 170 directly over target 161, as previously described, and by disposing the first end 171 of displacement bar 170 a vertical distance D' from the target 161 (as shown in FIG. 7). and by having distance D' be equal to the fixed radius of curvature R of arc bar 250, target 161 can be intersected by a medical instrument which passes from any location along arc bar 250 a distance equal to the fixed radius of curvature R of the arc bar 250. Thus, once the first end 171 of displacement bar 170 is disposed directly above target 161 a vertical distance D'. equal to the radius of curvature R of the arc bar, arc bar 250 may be rotated about its axis of rotation 258 (FIG. 11) to any angular disposition with respect to displacement bar 170, or arc bar 250 can be moved with respect to mounting block 251 within passageway 252, or medical instrument guide mounting bracket 260 can be moved to any position along arc bar 250, the medical instrument 181 passing through guide 261 a distance equal to the fixed radius of curvature R of arc bar 250 will always intercept the target 161 within skull 160. Thus, medical instrument 181 can pass through a variety of different locations on the surface of the skull in order to intersect target 161, such location being able to be chosen by the surgeon to provide the most efficient and expeditious entry through the skull 160 to intersect target 161.

With reference to FIGS. 7 and 11, it is seen that by being able to determine the distance D" between the reference point 303, or skull mount fixture 162 and target 161, subtracting that distance D" from the length of the fixed radius of curvature R of arc member 250, the distance D'" can be determined. This distance D'" provides the distance between the skull mount fixture 162 and the displacement bar 170, which distance D'" is secured by setting the depth stop 191 on post 163, upon which displacement bar 170 rests.

Figure 3:
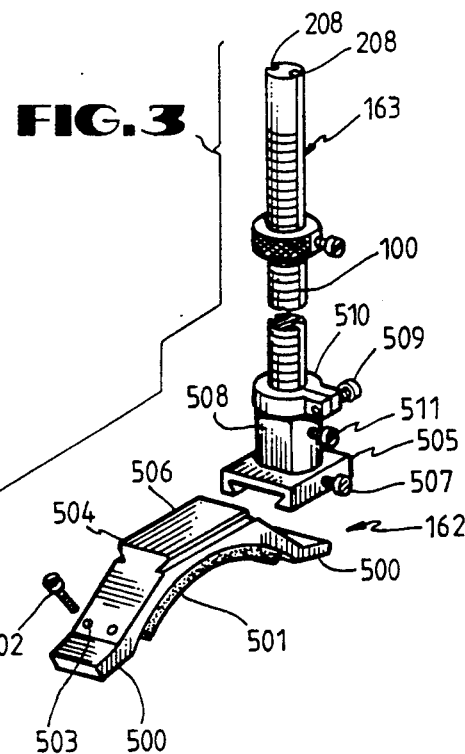
FIG. 3 is a perspective view of a skull mount fixture in accordance with the present invention.

With reference to FIGS. 3, and 11, a preferred form of skull mount fixture 162 will be described in greater detail. Skull mount fixture 162 has a rounded configuration to generally conform to the shape of the skull 160, with outwardly extending flanges 500 to provide additional rigidity and support for the skull mount fixture upon skull 160. A layer of foam material 501 may be provided to cushion skull mount fixture 162 upon the skull 160. A plurality of conventional bone screws 502 may be provided to secure skull mount fixture 162 to skull 160, a plurality of openings 503 being provided for the passage of bone screws 502. Alignment rod, or post, 163 may be formed integral with the upper surface 504 of skull mount fixture 162, or alternatively post 163 may be provided with grooved base number 505 which cooperates and mates with a tongue surface 506 disposed on the top surface 504 of skull mount fixture 162, so that post 163 can be readily removed from skull mount fixture 162. A conventional lockscrew 507 may be provided in base number 505 to secure it to skull mount fixture 162. Other conventional connections could, of course, be used to join post 163 to skull mount fixture 162. Base number 505 may include an upwardly extending receptacle 508 for receipt of post 163. Lockscrew 509 and clamp 510 secure post 163 with respect to base number 505 and lockscrew 511 cooperates with keyway 208 as previously described, to maintain the necessary orientation between guide bar 201 and post 163.

When the patient is being scanned, as previously described in connection with FIG. 1, alignment rod, or post 163, may be utilized, and the same post 163, and skull mount fixture 162 may be utilized in the subsequent stereotactic procedure, or a new post, or alignment rod, 163 may be later utilized.

Figure 4:
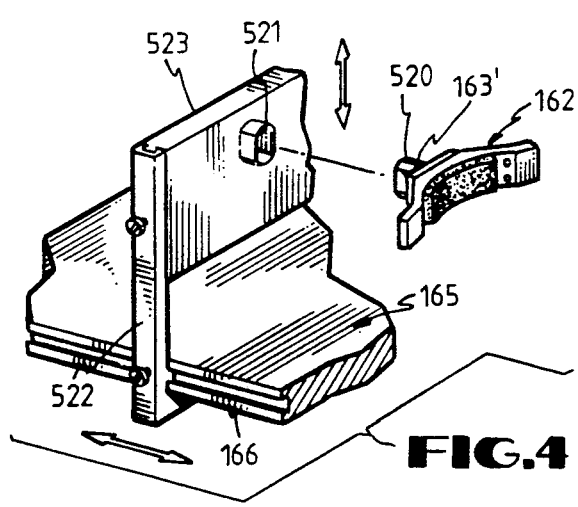
FIG. 4 is a perspective view of a skull mount fixture, cooperating and mating with a support surface.

In FIGS. 2 and 4, an alternative alignment rod 163' is shown used in connection with the skull mount fixture 162 of FIG. 3. Instead of the patient being held in position for the scanning procedure by the use of post 163 and bracket 167, alignment rod 163' may be disposed on skull mount fixture 162, via the previously described tongue and groove connection 505, 506. Alignment rod 163' comprises a raised boss 520 which mates with a cooperating cavity 521 which is adjustably mounted for movement in the horizontal and vertical directions to imaging table 166, as by movable, vertical bracket supports 522 which support a movable boss cavity member 523. When utilizing the alignment rod 163' of FIGS. 2 and 3, an alignment rod, or post 163 as previously described, is substituted for the alignment rod 163', after the scanning procedure has been accomplished.

Figure 5:
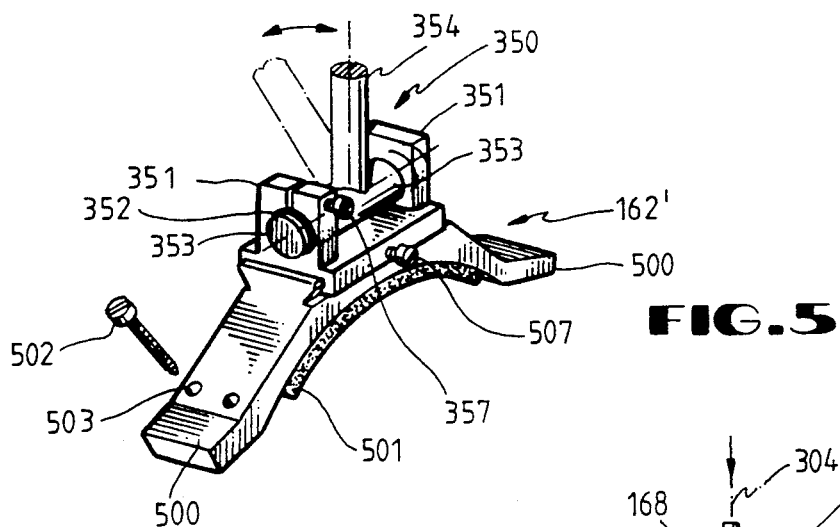
FIG. 5 is a perspective view of another embodiment of a skull mount fixture in accordance with the present invention.

With reference to FIGS. 5 and 8, another embodiment of a skull mount fixture 162 for use in linear offset applications is shown. Skull mount fixture 162' includes means for rotably mounting 350 a post 163. Skull mount fixture 162' has the same configuration as the lower part of skull mount fixture 162 previously described in connection with FIGS. 3 and 11. A base member 505, along with locking screw 507 is also provided, and base member 505 has two upstanding flange members 351 provided with bearings 352 for a rotatable rod, or shaft, 353, to which is fixedly secured an upstanding elongate, circular boss 354. A lockscrew 357 is provided for fixedly securing the position of rod 353 within bearings 352. Boss 354 may either be fixedly secured to rod, or shaft, 353 or alternatively a post 163, as previously described, can have its lower end bored out to accommodate boss 354 and be fixedly secured thereto as by a conventional lockscrew. Thus, skull mount fixture 162' permits angular offsetting of post 163 from its first position, previously described as being disclosed in a plane which is perpendicular to the planes in which lie the skull mount fixture 162 and displacement bar 170, to a second position, wherein the displacement bar 170 lies in a plane perpendicular to the angularly offset post 163. As seen in FIG. 8, by using the modified skull mount fixture 162', and by angularly offsetting boss 354 and post 163, the location of the target may be determined, which target lies in a plane which is not parallel to the planes in which lie the scanned images. As seen in FIG. 8, target 361' lies in angularly offset plane 375E. By utilizing skull mount fixture 162' in conjunction with the components previously described in connection with FIGS. 9 and 11, wherein post 163 is angularly offset as illustrated in FIG. 8, many functional procedures, as previously described, can be easily performed.

Figure 12:
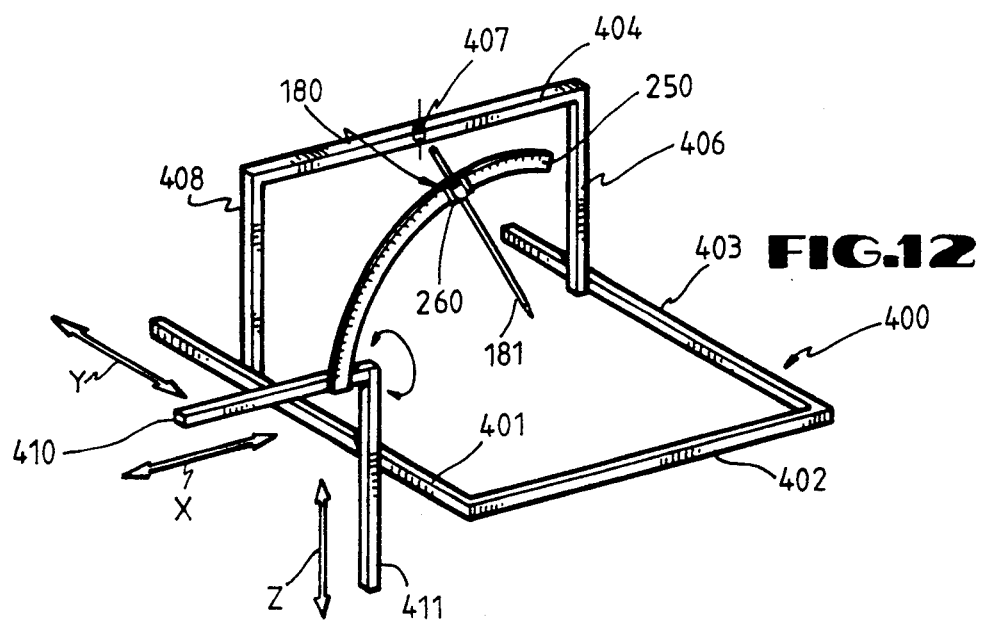
FIG. 12 is a perspective view of another system for performing stereotactic surgery in accordance with the present invention.
Figure 13:
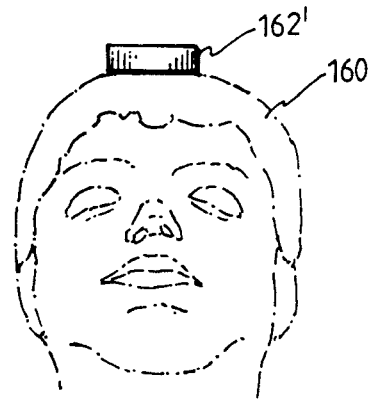
FIGS. 13-15 illustrate a patient having a stereotactic procedure conducted, utilizing the system illustrated in FIG. 12.
Figure 14:
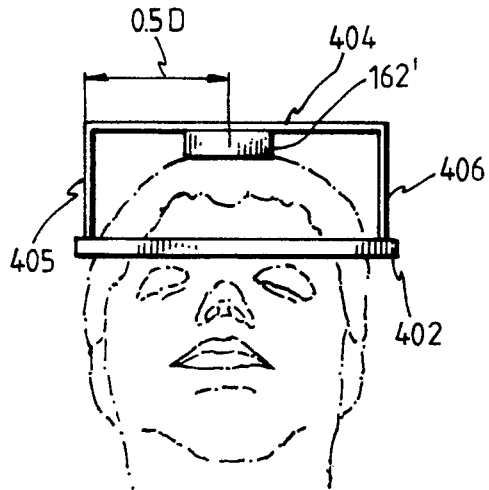

With reference to FIGS. 12-15, another embodiment of the method for performing stereotactic surgery of the present invention and apparatus therefor are illustrated. In FIG. 13, a patient is shown with a skull mount fixture 162' as previously described, disposed upon the patient's skull 160. As in the prior method, a first predetermined geometric relationship between the skull mount 162', which is attached to both the skull and to a support surface upon which the skull is disposed, and the support surface is established as previously described in connection with FIGS. 1 and 6. The skull 160 is scanned in the same manner as previously described in connection with FIGS. 1 and 6, and the linear coordinates of a target 161 are likewise determined as previously discussed in connection with FIG. 7. Instead of disposing a displacement bar 170 upon the skull mount fixture 162', a rectangular shaped frame structure 400 (FIG. 12) is disposed upon skull mount fixture 162' as seen in FIG. 14.

Rectangular shaped frame structure 400 preferably includes three bar members 401-403 which form a generally U-shaped frame, frame members 401 and 403 being disposed perpendicular to frame member 402. Frame members 401-403 are suspended from a horizontal frame support member 404 via two depending support members 405, 406. Horizontal support member 404 has an opening formed at its center, on the underside thereof, which opening 407 mates with upstanding boss 354 of skull mount fixture 162' (FIG. 5). As previously described in connection with the prior embodiment of the method for performing stereotactic surgery in accordance with the present invention, the first predetermined geometric relationship is with the skull mount fixture 162' disposed in a plane which lies perpendicular with respect to the longitudinal axis 301 of the support surface 165, and the second, predetermined geometric relationship is the frame structure 400 being disposed in a plane parallel with the plane in which lies the skull mount fixture 162', as seen in FIG. 14. Thus, the scanned images, or slices, 302A-302H, all lie in planes parallel with the planes in which lie the skull mount fixture 162' and the frame structure 400.

Figure 15:
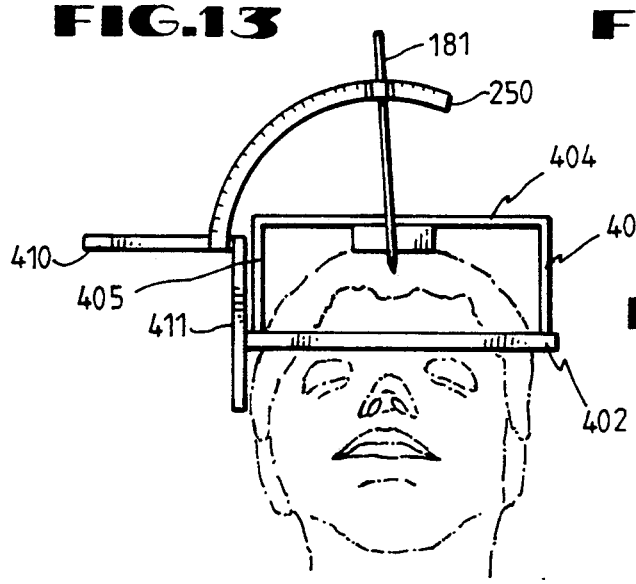

Two straight, elongate first and second coordinate bars 410, 411 are movably mounted to the frame structure 400, the coordinate bars 410, 411, being disposed perpendicular to each other and the first coordinate bar 410 is disposed in a plane parallel with the plane in which lies the skull mount fixture 162', as seen in FIGS. 14 and 15. First coordinate bar 410 is movably mounted for movement in the vertical direction, or along the Z axis, along the length of second coordinate bar 411, as shown in FIG. 12, and coordinate bar 411 is mounted for movement along the Y axis along member 401, as well as may be mounted for vertical movement along the Z axis with respect to member 401 in a conventional manner.

A means for guiding a medical instrument 180, or guide mounting bracket 260 and guide means 261, as previously described in FIG. 11, is movably mounted on an arc bar 250, as previously described in connection with FIG. 11. Arc bar 250 also has a fixed radius of curvature R. the arc bar being movably mounted on the first coordinate bar 410 for movement in the X direction. Upon proper positioning of the first and second coordinate bars 410. 411 along with arc bar 250, a medical instrument 181 may be passed through medical instrument guide means 180 to intersect a target 161 located within the patient's skull 160. By knowing the linear coordinates of the target 161 with respect to the skull mount fixture 162' as previously discussed in connection with FIG. 7, and by further knowing the distance that the first and second coordinate bars 410, 411 are offset from the skull mount fixture 162', or distance OSD in FIG. 14, coordinate bars 410. 411 and arc bar 250, can be positioned so that the desired target may be intersected by medical instrument 181. If it is desired to perform linear offset application, as previously described, the frame structure 400 may be rotated about skull mount fixture 162' via use of the skull mount fixture 162' as previously described in connection with FIGS. 5 and 8. Accordingly, boss 354 which mates with horizontal support bar 404 would be rotated to cause frame structure 400 to lie in a plane which is not parallel to the planes in which the scanned images lie as previously described in connection with FIG. 8. The frame 400 may also be provided with holders 415 to accept retractors and other medical or electrical equipment.

All of the components previously described in connection with FIGS. 1-15 may be made of any suitable material having the requisite strength characteristics and the ability to be sterilized may be used. Examples of such materials are aluminum, stainless steel, titanium, various plastic and/or carbon-fiber materials. Many of the various concepts can also have other cross sectional configurations from those illustrated.

It is to be understood that the invention is not limited to the exact details of construction, operation. exact materials, or embodiments shown and described as obvious modifications and equivalents will be apparent to one skilled in the art; for example, the skull mount fixture could have a generally circular, convex configuration. rather than a generally rectangular, convex configuration. Accordingly, the invention is therefore to be limited only by the scope of the appended claims.

I claim:

1. A method for performing stereotactic surgery with a medical instrument upon a target within a skull comprising the steps of:
   (a) establishing a first, predetermined geometric relationship between a skull mount fixture, attached to both the skull and to a support surface upon which the skull is disposed, and the support surface;
   (b) scanning the skull to produce images of the skull mount fixture and the target within the skull;
   (c) determining the linear coordinates of the target along X, Y and Z axes with respect to the skull mount fixture;
   (d) disposing a displacement bar, having first and second ends upon the skull mount fixture to establish a second, predetermined geometric relationship therebetween, which is identical to the first, predetermined geometric relationship;
   (e) disposing the first end of the displacement bar directly over the target in the skull;
   (f) associating a means for guiding a medical instrument with the first end of the displacement bar; and
   (g) inserting the medical instrument through the means for guiding a medical instrument, whereby the medical instrument will intersect the target in the skull.

2. The method of claim 1, wherein the first, predetermined geometric relationship is the skull mount fixture disposed in a plane which lies perpendicular with respect to the longitudinal axis of the support surface; and the second, predetermined geometric relationship is the displacement bar disposed in a plane parallel with the plane in which lies the skull mount fixture, whereby the scanned images all lie in planes parallel with the planes in which lie the skull mount fixture and the displacement bar.

3. The method of claim 2, including the steps of securing in a first position the first end of an elongate post, having first and second ends, to the skull mount fixture and releasably securing the displacement bar with respect to the second end of the post along the post; the post, in the first position, being disposed in a plane which is perpendicular to the planes in which lie the skull mount fixture and the displacement bar.

4. The method of claim 3, including the step of utilizing two cooperating guide bars to dispose the first end of the displacement bar directly over the target in the skull, one of the guide bars being associated with the linear coordinate of the target along the X-axis, and the other guide bar being associated with the linear coordinate of the target along the Y-axis.

5. The method of claim 4, wherein each guide bar has first and second ends, and the first end of one guide bar is fixedly secured to the post and the first end of the other guide bar is movably mounted on the first end of the displacement bar.

6. The method of claim 5, including the step of interconnecting the guide bars to one another intermediate the first and second ends of each guide bar, the guide bars being movable with respect to one another, whereby movement of one guide bar causes the first end of the displacement bar to move.

7. The method of claim 1, including the steps of movably mounting an arc bar, having a fixed radius of curvature, to the first end of the displacement bar; and movably mounting the medical instrument guide means upon the arc bar, whereby the target in the skull may be intersected by a medical instrument that has the capability to pass through the skull from a variety of different locations on the surface of the skull, dependent upon the locations of the arc bar with respect to the displacement bar and the medical instrument guide means with respect to the arc bar.

8. The method of claim 3, further including the steps of angularly offsetting the post from its first position to a second position, the displacement bar lying in a plane which is perpendicular to the angularly offset post, whereby the location of a target may be determined, which target lies in a plane which is not parallel to the planes in which lie the scanned images.

9. A system for performing stereotactic surgery with a medical instrument upon a target within a skull, comprising:
   (a) a skull mount fixture, having associated therewith a means for attaching the skull mount fixture to both the skull and to a support surface upon which the skull is disposed;
   (b) a straight, elongate displacement bar, having first and second ends, movably mounted upon the skull mount fixture for both longitudinal and rotational movement with respect to the skull mount fixture, the longitudinal axis of the displacement bar being disposed in a plane which lies parallel to the plane in which lies the longitudinal axis of the skull mount fixture; and
   (c) a means for guiding a medical instrument, the means for guiding a medical instrument being associated with the first end of the displacement bar.

10. The system of claim 9, wherein the skull mount fixture further includes an elongate post having first and second ends, the first end being secured to the skull mount fixture, the post lying in a plane which is perpendicular to the planes in which lie the longitudinal axes of the skull mount fixture and the displacement bar, the displacement bar being releasably secured with respect to the second end of the post.

11. The system of claim 10, including first means for adjustably securing the displacement bar along the length of the post in order to vary the distance of the displacement bar from the skull mount fixture.

12. The system of claim 10, including second means for securing the displacement bar to the post, whereby the distance from the first end of the displacement bar to the post may be varied.

13. The system of claim 10, including two cooperating guide bars, each guide bar having first and second ends; the first end of one guide bar being fixedly secured to the post and the first end of the other guide bar being movably mounted to the first end of the displacement bar; the guide bars are interconnected to one another intermediate the first and second ends of each guide bar; and the guide bars being movable with respect to each other, whereby movement of the guide bar mounted to the first end of the displacement bar causes the displacement bar to move longitudinally and rotationally with respect to the post.

14. The system of claim 13, further comprising an arc bar, having a fixed radius of curvature, the arc bar is movably mounted to the first end of the displacement bar; and the medical instrument guide means is movably mounted upon the arc bar.

15. The system of claim 10, including a protractor plate secured to the post to determine the angular orientation of the longitudinal axis of the displacement bar with respect to the longitudinal axis of the post.

16. The system of claim 15, wherein an arc bar, having a fixed radius of curvature is movably mounted to the first end of the displacement bar; and the medical instrument guide means is movably mounted upon the arc bar.

17. The system of claim 10, wherein the post is rotatably mounted and secured to the post, whereby the post may be rotated and the longitudinal axis of the displacement bar can be caused to lie in planes which are not parallel to the plane in which lies the longitudinal axis of the skull mount fixture.

* * * * *